(12) United States Patent
Takemoto et al.

(10) Patent No.: US 10,041,909 B2
(45) Date of Patent: Aug. 7, 2018

(54) PORTABLE ULTRASONIC TESTING DEVICE AND ULTRASONIC TESTING METHOD

(71) Applicant: MITSUBISHI HEAVY INDUSTRIES, LTD., Tokyo (JP)

(72) Inventors: Hiroshi Takemoto, Tokyo (JP); Kazuhiro Ueshiro, Tokyo (JP); Tadayoshi Kimura, Hyogo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 162 days.

(21) Appl. No.: 15/027,249

(22) PCT Filed: Sep. 3, 2014

(86) PCT No.: PCT/JP2014/073255
§ 371 (c)(1),
(2) Date: Apr. 5, 2016

(87) PCT Pub. No.: WO2015/060020
PCT Pub. Date: Apr. 30, 2015

(65) Prior Publication Data
US 2016/0231283 A1 Aug. 11, 2016

(30) Foreign Application Priority Data

Oct. 23, 2013 (JP) ................................ 2013-220591

(51) Int. Cl.
*G01N 29/04* (2006.01)
*G01N 29/265* (2006.01)
(Continued)

(52) U.S. Cl.
CPC ........... *G01N 29/04* (2013.01); *G01N 29/043* (2013.01); *G01N 29/225* (2013.01);
(Continued)

(58) Field of Classification Search
CPC .... G01N 29/04; G01N 29/043; G01N 29/226; G01N 29/24; G01N 29/265; G01N 29/11; G01N 29/262; G01N 29/225
See application file for complete search history.

(56) References Cited

U.S. PATENT DOCUMENTS

| | | | | |
|---|---|---|---|---|
| 4,807,476 A | * | 2/1989 | Cook ................. | G01N 29/0645 73/620 |
| 5,698,787 A | * | 12/1997 | Parzuchowski .... | G01N 29/2418 73/583 |

(Continued)

FOREIGN PATENT DOCUMENTS

| | | |
|---|---|---|
| EP | 2437053 A1 | 4/2012 |
| JP | 58-178672 U | 11/1983 |

(Continued)

OTHER PUBLICATIONS

Written Opinion of the ISA in PCT/JP2014/073255, dated Dec. 2, 2014.

(Continued)

*Primary Examiner* — Helen Kwok
(74) *Attorney, Agent, or Firm* — Hauptman Ham, LLP

(57) ABSTRACT

A portable ultrasonic testing device which with respect to a plate material having a chamfered surface formed between an outer plate surface and an inner peripheral surface, irradiates the chamfered surface with ultrasonic waves while moving along the chambered surface to thereby detect flaws in the plate material is provided with: a device frame; a probe which irradiates the chambered surface with the ultrasonic waves, and receives reflected ultrasonic waves; a wedge to which the probe is fixed and which is able to come into contact with the chamfered surface; a slide mechanism which moves the wedge in a sliding direction with respect to the device frame; a spring member which is urged in a direction in which the wedge and the chamfered surface (Continued)

approach each other in the sliding direction; and a movable roller and a pair of fixed rollers which are provided in the device frame and each have a rolling contract surface that is in contact with the inner peripheral surface.

11 Claims, 4 Drawing Sheets

(51) Int. Cl.
*G01N 29/22* (2006.01)
*G01N 29/24* (2006.01)

(52) U.S. Cl.
CPC ........... *G01N 29/226* (2013.01); *G01N 29/24* (2013.01); *G01N 29/265* (2013.01); *G01N 2291/044* (2013.01); *G01N 2291/106* (2013.01)

(56) References Cited

U.S. PATENT DOCUMENTS

| | | | | |
|---|---|---|---|---|
| 7,334,341 | B2* | 2/2008 | Donaldson | G01B 21/047 33/286 |
| 8,087,298 | B1* | 1/2012 | DiMambro | G01N 29/226 73/629 |
| 2004/0089082 | A1* | 5/2004 | Gifford | G01N 27/902 73/866.5 |
| 2006/0042391 | A1* | 3/2006 | Georgeson | G01N 29/07 73/633 |
| 2006/0201252 | A1* | 9/2006 | Georgeson | G01N 29/041 73/641 |
| 2006/0243051 | A1* | 11/2006 | Bui | G01N 29/043 73/618 |
| 2007/0006657 | A1* | 1/2007 | Kennedy | G01N 29/225 73/618 |
| 2007/0044562 | A1* | 3/2007 | Sarr | G01N 29/225 73/618 |
| 2007/0044563 | A1* | 3/2007 | Sarr | G01N 29/226 73/618 |
| 2008/0066553 | A1* | 3/2008 | Espada Tejedor | G01N 29/225 73/627 |
| 2010/0107768 | A1* | 5/2010 | Elze | G01N 29/043 73/627 |
| 2010/0198076 | A1* | 8/2010 | Kollgaard | G01N 29/225 600/459 |
| 2012/0060609 | A1* | 3/2012 | Fukutomi | G01N 29/225 73/592 |
| 2013/0220018 | A1* | 8/2013 | Kollgaard | G01N 29/04 73/618 |
| 2013/0289766 | A1* | 10/2013 | Hafenrichter | B25J 9/02 700/245 |
| 2015/0153310 | A1* | 6/2015 | Yamamoto | G01N 29/0645 73/627 |

FOREIGN PATENT DOCUMENTS

| | | |
|---|---|---|
| JP | 6-64154 U | 9/1994 |
| JP | 6-331610 A | 12/1994 |
| JP | 8-15478 A | 1/1996 |
| JP | 2001-194352 A | 7/2001 |
| JP | 2003-270224 A | 9/2003 |
| JP | 2007-46945 A | 2/2007 |
| JP | 4961051 B2 | 6/2012 |
| JP | 2012-255776 A | 12/2012 |
| JP | 2013-113708 A | 6/2013 |

OTHER PUBLICATIONS

International Search Report in PCT/JP2014/073255, dated Dec. 2, 2014.
Extended European Search Report in EP Application No. 14855000.7, dated Nov. 9, 2016.
Office Action in JP Application No. 2013-220591, dated Apr. 11, 2017.

* cited by examiner

PORTABLE ULTRASONIC TESTING DEVICE AND ULTRASONIC TESTING METHOD

RELATED APPLICATIONS

The present application is a National Stage of PCT International Application No. PCT/JP 2014/073255, filed Sep. 3, 2014 which claims the benefit of priority from Japanese Patent Application No. 2013-220591, filed Oct. 23, 2013.

TECHNICAL FIELD

The present invention relates to a portable ultrasonic testing device that detects flaws in an object to be inspected by irradiating the object to be inspected with ultrasonic waves, and to an ultrasonic testing method using the same.

BACKGROUND ART

An ultrasonic testing device that inspects joint portions of a quadrangular pillar body by scanning the body with a first probe and a second probe, and a scanner having a three-axis drive shaft is known as a conventional ultrasonic testing device (see Patent Document 1, for example). In this ultrasonic testing device, the probes irradiate an outer surface of the quadrangular pillar body with ultrasonic waves.

CITATION LIST

Patent Literature

Patent Document 1: Japanese Unexamined Patent Application Publication No. 2007-46945A

SUMMARY OF INVENTION

Technical Problem

Incidentally, in addition to a flat outer surface of the quadrangular pillar body as described in Patent Document 1, a chamfered surface having a curved surface formed at peripheral edge portions of through-holes and the like can also serve as a surface to be inspected of the object to be inspected irradiated with ultrasonic waves. In Patent Document 1, the scanner is attached on an outer side of the quadrangular pillar body, but it is difficult to attach the scanner in the case where the surface to be inspected is a curved surface. There are also cases where the curved surface serving as the surface to be inspected will have a different radius of curvature depending on the position where flaws are to be detected. Thus even if the scanner can be attached, it will be necessary to appropriately correct the positions of the probes in accordance with the radius of curvature of the curved surface, which complicates the flaw detection operation.

In such a case, it is conceivable to use a portable ultrasonic testing device to irradiate the curved surface serving as the surface to be inspected with ultrasonic waves. However, the position of a probe cannot be fixed relative to the surface to be inspected, and thus it is difficult to maintain the positional relationship between the surface to be inspected and the probe while moving the probe along the surface to be inspected. This results in the surface to be inspected being irradiated with the ultrasonic waves at different irradiation angles. This in turn causes variations in the irradiation conditions of the ultrasonic waves with which the surface to be inspected is irradiated, making it difficult to accurately detect flaws within the object to be inspected. In particular, in the case where the object to be inspected is a material having acoustical anisotropy, even a slight variation in the irradiation angle of the ultrasonic waves will result in variations in the sonic velocity of the ultrasonic waves propagating within the object to be inspected, which may cause error to arise in the detection results obtained from the flaw detection.

Accordingly, an object of the present invention is to provide a portable ultrasonic testing device and an ultrasonic testing method capable of accurately detecting flaws within an object to be inspected by moving a probe along the shape of a surface to be inspected in a favorable manner while maintaining a positional relationship between the object to be inspected and the probe.

Solution to Problem

A portable ultrasonic testing device, with respect to an object to be inspected having a surface to be inspected formed between a first surface and a second surface, irradiates the surface to be inspected with ultrasonic waves while moving along the surface to be inspected so as to detect flaws in the object to be inspected. Such a device includes: a device frame; a probe that irradiates the surface to be inspected with the ultrasonic waves and receives reflected ultrasonic waves; a wedge to which the probe is fixed and that is able to come in contact with the surface to be inspected; a slide mechanism that moves the wedge in a sliding direction with respect to the device frame; an urging member that urges the wedge so that the wedge and the surface to be inspected approach each other in the sliding direction; and a guide member that is provided in the device frame and has a second contact surface that comes into contact with the second surface.

According to this configuration, the guide member can be brought into contact with the second surface of the object to be inspected, the wedge can be brought into contact with the surface to be inspected of the object to be inspected, and the urging member can apply an urging force to the wedge. A state of contact between the surface to be inspected and the wedge can therefore be maintained, and thus a positional relationship between the surface to be inspected of the object to be inspected and the probe fixed to the wedge can be maintained even in the case where the wedge is moved along the surface to be inspected with the guide member in contact with the object to be inspected. Through this, the probe can move in a favorable manner along the shape of the surface to be inspected, and thus flaws within the object to be inspected can be detected with a high level of accuracy.

In addition, it is preferable that the device further include a wedge guide that with respect to the device frame, moves in the sliding direction along with the wedge and that has a first contact surface that comes into contact with the first surface.

According to this configuration, the wedge guide can be brought into contact with the first surface of the object to be inspected, and thus the position of the ultrasonic testing device 1 in a direction orthogonal to the first surface can be regulated. Accordingly, by bringing the wedge guide into contact with the first surface of the object to be inspected, the positional relationship between the surface to be inspected and the probe can be maintained more favorably, even in the case where the wedge is moved along the surface to be inspected.

In addition, it is preferable that the wedge guide be provided extending on both sides of the wedge in an orthogonal direction orthogonal to the sliding direction within the first contact surface.

According to this configuration, the wedge guide can be formed having a broad shape that widens on both sides of the wedge, and thus the surface area across which first surface of the object to be inspected and the first contact surface of the wedge guide come into contact can be increased. Accordingly, the object to be inspected and the wedge guide can be brought into stable contact with each other, and thus the wedge can be moved along the surface to be inspected in a stable manner.

In addition, it is preferable that the object to be inspected be a plate material in which a through-hole is formed, the first surface be a plate surface of the plate material, the second surface be an inner peripheral surface of the through-hole, and the surface to be inspected be a chamfered surface formed by chamfering a peripheral edge of the through-hole.

According to this configuration, flaws within the object to be inspected under the chamfered surface formed in the peripheral edge portion of the through-hole can be detected with a high level of accuracy.

In addition, it is preferable that the object to be inspected be a composite material.

According to this configuration, it is possible to maintain a positional relationship between the probe and the surface to be inspected of the object to be inspected such that the irradiation angle of the ultrasonic waves emitted from the probe onto the composite material, which is a material having acoustical anisotropy, becomes an irradiation angle suitable for ultrasonic testing. As such, this configuration is particularly useful in the case where the object to be inspected is a composite material. A fiber-reinforced plastic such as CFRP is an example of the composite material.

In addition, it is preferable that the guide member be a rolling contact member that is attached to the device frame and has a rolling contact surface as the second contact surface that comes into contact with the second surface.

According to this configuration, a rolling contact member can be used as the guide member, and thus in the case where the wedge is moved along the surface to be inspected, contact resistance between the second surface of the object to be inspected and the rolling contact surface of the rolling contact member can be reduced, which makes it possible to carry out smooth movement along the second surface. Note that the rolling contact member may be a circular pillar-shaped roller that makes linear contact with the second surface, a ball roller that makes point contact with the second surface, or the like.

In addition, it is preferable that the rolling contact member include: a movable roller provided in the device frame, the movable roller including a rotation shaft that moves in the same direction as the sliding direction; and a pair of fixed rollers provided in the device frame so as to be located on both sides of the rotation shaft of the movable roller in a radial direction, the fixed rollers including fixed rotation shafts.

According to this configuration, in the case where the second surface of the object to be inspected is a curved surface having a varying radius of curvature, the movable roller present between the pair of fixed rollers moves in the sliding direction in accordance with the radius of curvature, and thus the movable roller and the pair of fixed rollers can be moved along the second surface, which is a curved surface, in a favorable manner.

In addition, it is preferable that the device further include a rotational position detector that is connected to the rolling contact member and is capable of detecting a rotational position of the rolling contact member.

According to this configuration, connecting the rolling contact member to the rotational position detector makes it possible to associate the rotational position detected by the rotational position detector with the flaw detection result obtained by the probe at that rotational position. Accordingly, the flaw detection result from the probe can be expanded in the movement direction in which the wedge moves along the surface to be inspected and mapped. Note that in the case where the probe is constituted of a single ultrasonic element, a linear map extending in the movement direction is generated, whereas in the case where the probe is an array-type probe constituted of a plurality of ultrasonic elements, a plane-shaped map expanded in the array direction and the movement direction is generated. Note also that a rotary encoder, for example, is used as the rotational position detector.

In addition, it is preferable that the wedge have a detecting surface that comes into contact with the surface to be inspected of the object to be inspected, and that the device further include a medium storage unit that is formed as a depression with respect to the detecting surface of the wedge and that holds a propagation couplant to be located between the probe and the surface to be inspected.

According to this configuration, the medium storage unit is formed as a depression with respect to the detecting surface of the wedge. Accordingly, by holding the propagation couplant in the medium storage unit, the propagation couplant can be located between the probe and the surface to be inspected of the object to be inspected without a gap being present therebetween. As a result, it is possible to suppress the sonic velocity from varying due to such a gap between the probe and the surface to be inspected, which in turn makes it possible to suppress a drop in the flaw detection accuracy due to variations in the sonic velocity. Note that water is an example of the propagation couplant.

In addition, it is preferable that the probe be an array-type probe in which ultrasonic elements that transmit and receive ultrasonic waves are arranged in a direction that connects the first surface and the second surface.

According to this configuration, the surface to be inspected can be irradiated with the ultrasonic waves across the width direction thereof by using the array-type probe. Accordingly, flaws within the object to be inspected under the surface to be inspected can be detected with efficiency by moving the wedge along the surface to be inspected, and thus the flaw detection operation can be simplified.

In addition, it is preferable that the probe emit the ultrasonic waves across both the surface to be inspected and the first surface, and irradiate the surface to be inspected with the ultrasonic waves so as to achieve an angle of incidence calculated on the basis of the sonic velocity of the ultrasonic waves with which the surface to be inspected is irradiated, the sonic velocity of the ultrasonic waves with which the surface to be inspected is irradiated and that propagate within the object to be inspected, and an angle of diffraction at the surface to be inspected.

According to this configuration, an angle formed between the probe and the surface to be inspected of the object to be inspected is a different angle from the angle formed between the probe and the first surface of the object to be inspected. At this time, the sonic velocity of the ultrasonic waves with which the first surface is irradiated (the sonic velocity of the ultrasonic waves in the propagation couplant, for example)

is a different sonic velocity from the sonic velocity with which the first surface is irradiated and that propagate within the object to be inspected. Likewise, the sonic velocity of the ultrasonic waves with which the surface to be inspected is irradiated (the sonic velocity of the ultrasonic waves in the propagation couplant, for example) is a different sonic velocity from the sonic velocity with which the surface to be inspected is irradiated and that propagate within the object to be inspected. Accordingly, the probe calculates an angle of incidence θ on the basis of Snell's law, using the sonic velocity of the ultrasonic waves in the propagation couplant, the sonic velocity of the ultrasonic waves within the object to be inspected, and an angle of diffraction, and emits the ultrasonic waves so as to achieve the angle of incidence θ. As such, the probe can be attached taking into consideration variations in the sonic velocity caused by the refractive index between the propagation couplant and the object to be inspected, and thus flaws in the object to be inspected under the surface to be inspected can be detected at a high level of accuracy.

In addition, it is preferable that the device further include an attitude detector that measures an attitude of the probe, and an alarm that, on the basis of a measurement result from the attitude detector, makes a notification that the attitude of the probe with respect to the surface to be inspected of the object to be inspected in not suitable for flaw detection.

According to this configuration, in the case where the attitude of the probe is not suitable for flaw detection, that information can be communicated to an inspector by the alarm. Accordingly, the flaw detection can be suppressed from being carried out at an attitude not suitable for flaw detection, which makes it possible to carry out the flaw detection correctly. An accelerometer, a gyrosensor, or the like can be given as examples of the attitude detector, and such a detector may have two or three axes in accordance with the attitude of the probe to be measured. An attitude in a roll direction (direction of rotation) of the probe relative to the surface to be inspected, central to an axis orthogonal to the surface to be inspected, is an example of the attitude of the probe relative to the surface to be inspected. An attitude in an angle direction (tilt direction) of the probe relative to the surface to be inspected is an example of the attitude of the probe relative to the detecting surface. For example, a lamp, a speaker, or the like may be used as the alarm. Furthermore, the configuration may be such that the attitude of the probe (the wedge) is adjusted automatically or manually in accordance with the measurement result from the attitude detector.

An ultrasonic testing method according to the present invention is an ultrasonic testing method that detects flaws in the object to be inspected having the surface to be inspected using the aforementioned ultrasonic testing device. The method includes: a contact step of bringing the second contact surface of the guide member into contact with the second surface of the object to be inspected, bringing the wedge into contact with the surface to be inspected of the object to be inspected, and applying an urging force to the wedge using the urging member; and a movement step of moving the wedge along the surface to be inspected while the wedge and the guide member are in contact with the object to be inspected.

According to this configuration, in the contact step, the guide member can be brought into contact with the second surface of the object to be inspected, the wedge can be brought into contact with the surface to be inspected of the object to be inspected, and the urging member can apply an urging force to the wedge. Then, in the movement step, the wedge can be moved along the surface to be inspected in a state where the wedge and the guide member are in contact with the object to be inspected. Through this, the positional relationship between the surface to be inspected of the object to be inspected and the probe fixed to the wedge can be maintained even in the case where the wedge is moved along the surface to be inspected. Through this, the probe can move in a favorable manner along the shape of the surface to be inspected, and thus flaws within the object to be inspected can be detected with a high level of accuracy.

DESCRIPTION OF EMBODIMENTS

Detailed descriptions will be given below of embodiments according to the present invention on the basis of the drawings. Note that the present invention is not limited by these embodiments. In addition, the constituent elements in the embodiments described below include those that can be easily replaced by a person skilled in the art or those that are substantially the same.

EXAMPLES

Figure 1:
FIG. 1 is a cross-sectional view of an object to be inspected serving as an inspection target for a portable ultrasonic testing device according to an embodiment.
Figure 2:
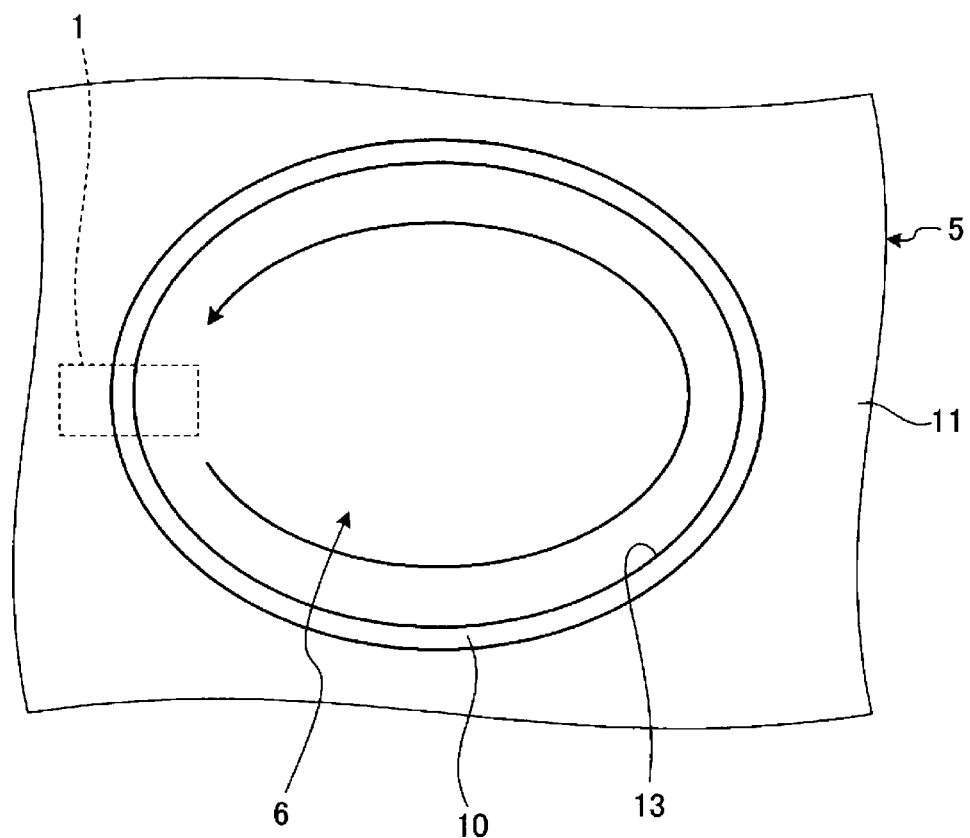
FIG. 2 is a plan view of an object to be inspected serving as an inspection target for the portable ultrasonic testing device according to the embodiment.
Figure 3:
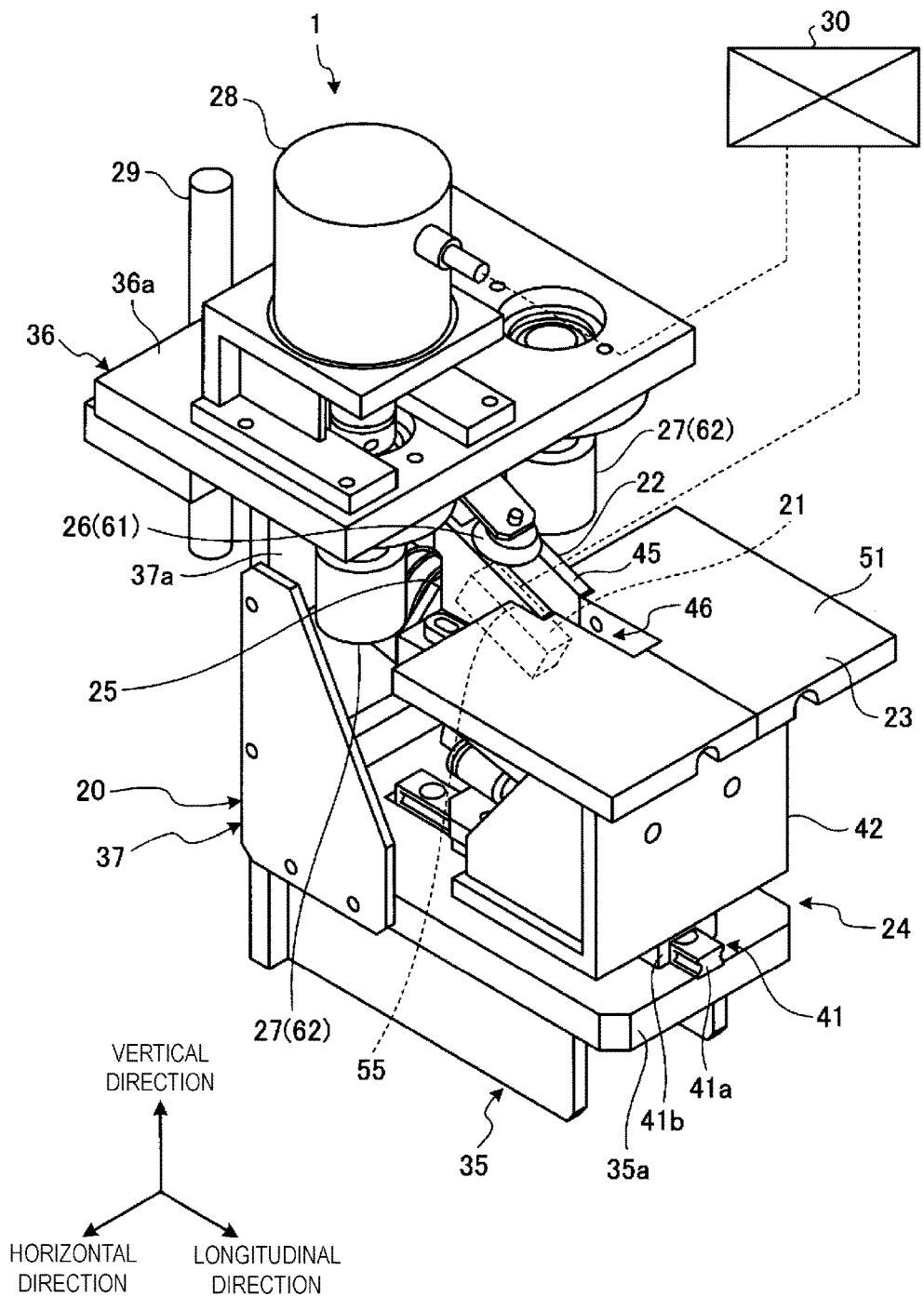
FIG. 3 is a perspective view of the portable ultrasonic testing device according to the embodiment.
Figure 4:
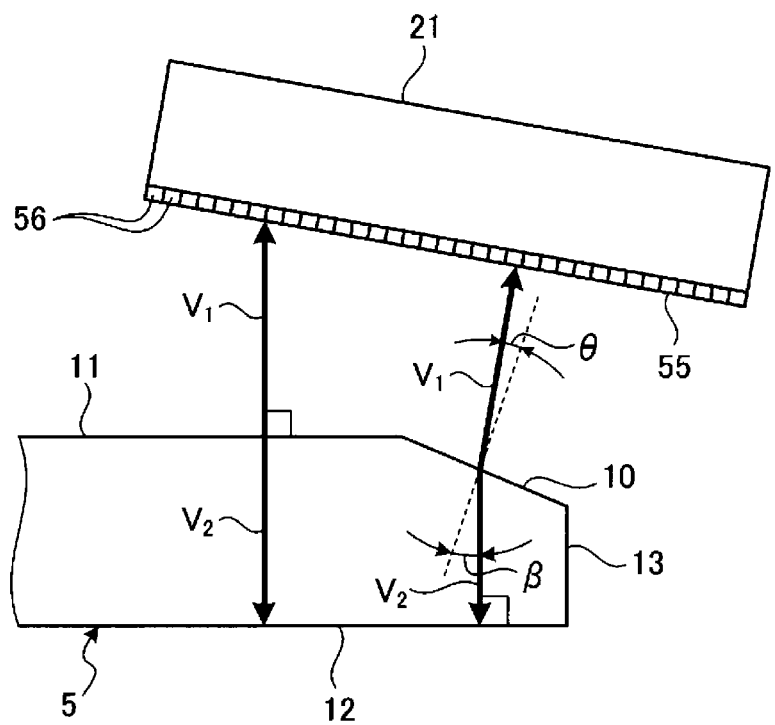
FIG. 4 is a schematic diagram illustrating ultrasonic wave sonic velocity correction.
Figure 5:
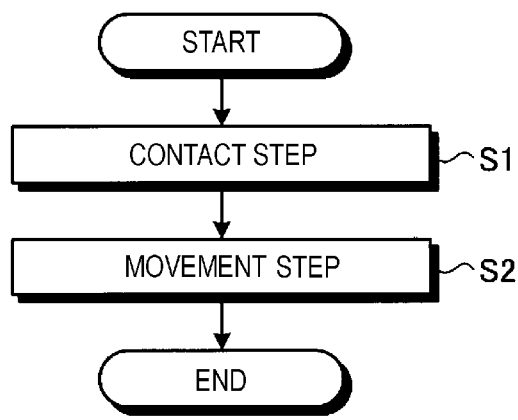
FIG. 5 is a flowchart illustrating an ultrasonic testing method that uses the portable ultrasonic testing device according to the embodiment.

FIG. 1 is a cross-sectional view of an object to be inspected serving as an inspection target for a portable ultrasonic testing device according to the present embodiment. FIG. 2 is a plan view of the object to be inspected serving as the inspection target for the portable ultrasonic testing device according to the present embodiment. FIG. 3 is a perspective view of the portable ultrasonic testing device according to the present embodiment. FIG. 4 is a schematic diagram illustrating ultrasonic wave sonic velocity correction. FIG. 5 is a flowchart illustrating an ultrasonic testing method that uses the portable ultrasonic testing device according to the present embodiment.

A portable ultrasonic testing device 1 according to the present embodiment detects flaws within an object to be inspected beneath a surface to be inspected by irradiating the surface to be inspected with ultrasonic waves from an ultrasonic wave probe 21 (called simply a "probe" hereinafter) while moving the probe 21 along the surface to be inspected of the object to be inspected. First, the object to be inspected, which serves as an inspection target, will be described with reference to FIGS. 1 and 2.

The object to be inspected is a plate material 5 in which a through-hole 6 is formed. The plate material 5 is formed from a composite material. Carbon fiber reinforced plastic (CFRP), for example, is used as the composite material. Although the object to be inspected is formed using CFRP in the present embodiment, it should be noted that the object to be inspected is not particularly limited, and another fiber-reinforced plastic, a metal material such as an aluminum alloy, or the like may be used as well. In addition, although the object to be inspected is described as a plate material in the present embodiment, the object to be inspected is not particularly limited to having a plate shape.

Here, the composite material is a material having acoustical anisotropy, and thus the sonic velocity of the ultrasonic waves propagating within the plate material 5 differs depending on the propagation direction (irradiation direction) thereof. Accordingly, in the case where the plate material 5 is formed using a material having acoustical anisotropy, the ultrasonic waves with which the plate material 5 is irradiated having different irradiation directions will cause an increase in error in the detection results obtained through the flaw detection. As such, it is preferable that the irradiation direction of the ultrasonic waves with which the plate material 5 is irradiated be a constant irradiation direction.

The plate material 5 is employed in the main wing of an aircraft, for example, with an upper surface of the plate material 5 serving as an inner plate surface 12 and a lower surface thereof serving as an outer plate surface 11. The through-hole 6 formed in the plate material 5 is used as an access hole through which a person enters and exits. As illustrated in FIG. 2, the through-hole 6 has an elliptical shape when viewed in plan view, and thus an inner peripheral surface 13 of the through-hole 6 is a curved surface whose radius of curvature varies. Note that as illustrated in FIG. 1, the outer plate surface 11 of the plate material 5 and the inner peripheral surface 13 of the through-hole 6 are surfaces that intersect at a right angle when the plate material 5 is viewed as a cross-section. Meanwhile, a chamfered surface 10 is formed by chamfering a peripheral edge portion of the through-hole 6.

The chamfered surface 10 is formed between the outer plate surface 11 and the inner peripheral surface 13, and is formed in an elliptical shape when viewed in plan view. Here, a direction that connects the outer plate surface 11 and the inner peripheral surface 13 is defined as a width direction of the chamfered surface 10, and a direction in which the chamfered surface 10 extends in defined as a length direction. The width direction and the length direction are orthogonal within the chamfered surface 10. Meanwhile, an angle formed between the chamfered surface 10 and the outer plate surface 11 is defined as an inclination angle.

Next, the ultrasonic testing device 1 will be described with reference to FIG. 3. The ultrasonic testing device 1 illustrated in FIG. 3 is a portable device. The ultrasonic testing device 1 is gripped by an inspector and moved along the length direction of the chamfered surface 10 in order to detect flaws in the plate material 5 under the chamfered surface 10. In other words, the chamfered surface 10 of the plate material 5 serves as the surface to be inspected.

As illustrated in FIG. 3, the ultrasonic testing device 1 includes a device frame 20, a probe 21, a wedge 22, a wedge guide 23, a slide mechanism 24, a spring member (urging member) 25, a movable roller 26, a pair of fixed rollers 27, an encoder (rotational position detector) 28, a handle 29, and a control unit 30.

The device frame 20 includes a lower frame 35, an upper frame 36, and a side frame 37 that connects the upper frame 36 and the lower frame 35. Here, a direction that connects the lower frame 35 to the upper frame 36 is defined as a vertical direction. The lower frame 35 includes a lower plate 35a, and the slide mechanism 24 is provided in this lower plate 35a. The side frame 37 is connected to the lower frame 35 on a lower side of the side frame 37, and extends from the lower frame 35 toward the upper frame 36. The side frame 37 includes a side plate 37a, and one end of the spring member 25 is connected to the side plate 37a. The upper side of the side frame 37 is connected to the upper frame 36. The upper frame 36 includes an upper plate 36a, and the movable roller 26, the pair of fixed rollers 27, the encoder 28, and the handle 29 are provided on this upper plate 36a.

The slide mechanism 24 is provided on an upper side of the lower plate 35a, and includes a linear slider 41 constituted of a stationary part 41a and a mobile part 41b, and a slide platform 42 provided on the linear slider 41. The stationary part 41a of the linear slider 41 is fixed to the lower plate 35a of the lower frame 35, and the mobile part 41b of the linear slider 41 moves along the stationary part 41a in a predetermined sliding direction. Here, the sliding direction of the linear slider 41 is defined as a longitudinal direction. The longitudinal direction and the vertical direction are orthogonal to each other. The slide platform 42 is attached to the top of the mobile part 41b.

The wedge 22 is fixed to the slide platform 42, and moves in the longitudinal direction along with the slide platform 42. The probe 21 is fixed inside the wedge 22, and a flat detecting surface 45 that makes contact with the chamfered surface 10 is formed on a top portion of the wedge 22. Meanwhile, part of a water storage unit (medium storage unit) 46 that stores water serving as a propagation couplant is formed in an upper portion of the wedge 22. The water storage unit 46 is formed as a depression with respect to the detecting surface 45, and is formed extending from the wedge 22 to the wedge guide 23. Water stored in the water storage unit 46 makes contact with the detecting surface 45 and the chamfered surface 10 so as to be located between the probe 21 and the chamfered surface 10.

The wedge guide 23 is provided so as to extend on both sides of a horizontal direction, which is orthogonal to the longitudinal direction and the vertical direction, with the wedge 22 located therebetween. As such, the wedge guide 23 is formed so that a width thereof in the horizontal direction is greater than a width of the wedge 22 in the horizontal direction. The wedge guide 23 is formed having a rectangular planar shape, is fixed directly or indirectly to the slide platform 42, and moves in the longitudinal direction along with the slide platform 42 and the wedge 22. A flat contact surface (first contact surface) 51 that makes contact with the outer plate surface 11 is formed in an upper portion of the wedge guide 23. Part of the above-described water storage unit 46 is formed in the upper portion of the wedge guide 23, and the water storage unit 46 is formed depression with respect to the contact surface 51.

Here, a positional relationship between the wedge 22 and the wedge guide 23 will be described. The detecting surface 45 of the wedge 22 is tilted relative to the contact surface 51 of the wedge guide 23, and the positional relationship between the wedge 22 and the wedge guide 23 is fixed. Note that the positional relationship between the wedge 22 and the wedge guide 23 is fixed so that an angle of attachment between the detecting surface 45 and the contact surface 51 is the same angle as the inclination angle between the chamfered surface 10 and the outer plate surface 11. However, the angle of attachment formed between the detecting surface 45 of the wedge 22 and the contact surface 51 of the wedge guide 23 can be adjusted. In other words, the position where the wedge 22 is attached to the slide platform 42 can be adjusted, and the angle of attachment can be adjusted by adjusting the attachment position of the wedge 22.

Note that there are some cases where the inclination angle between the chamfered surface 10 of the plate material 5 and the outer plate surface 11 is not constant. In this case, the positional relationship between the wedge 22 and the wedge guide 23 is fixed so that the angle of attachment between the detecting surface 45 and the contact surface 51 is the same angle as an inclination angle between the chamfered surface 10 and the outer plate surface 11 at which the inclination angle is the most obtuse.

The probe 21 is fixed within the wedge 22, and has formed thereon a transceiving surface 55 that irradiates the chamfered surface 10 with ultrasonic waves and receives reflected ultrasonic waves. The probe 21 is an array-type probe 21 in which a plurality of ultrasonic elements 56 are provided in an array in the transceiving surface 55. Here, a direction in which the plurality of ultrasonic elements 56 are arranged is defined as an array direction. The probe 21 is fixed within (the water storage unit 46 formed in) the wedge 22 so that the transceiving surface 55 of the probe 21 is located on an upper side thereof and so that the water stored in the water storage unit 46 is located between the transceiving surface 55 and the chamfered surface 10. Accordingly, the ultrasonic waves emitted from the probe 21 propagate from the bottom toward the top in FIG. 3. Note that the probe 21 is fixed in the wedge 22 so that the array direction matches the longitudinal direction.

Here, the probe 21 has a length in the array direction that spans from the chamfered surface 10 to the outer plate surface 11. Accordingly, both the chamfered surface 10 and the outer plate surface 11 are irradiated with the ultrasonic waves emitted from the probe 21. The probe 21 is connected to the control unit 30, and irradiation conditions of the ultrasonic waves and the like are controlled by the control unit 30.

The spring member 25 serves to urge the detecting surface 45 of the wedge 22 and the chamfered surface 10 of the plate material 5 toward each other in the longitudinal direction. Specifically, a compression spring, for example, is used as the spring member 25, with one end thereof being connected to the side plate 37a of the side frame 37 and the other end thereof being connected to the wedge 22. The spring member 25 urges the wedge 22 away from the device frame 20 in the longitudinal direction.

The movable roller 26 is attached on a lower side of the upper plate 36a of the upper frame 36, and a rotation shaft thereof is capable of moving in the longitudinal direction. The movable roller 26 is formed having a circular pillar shape, and has a rolling contact surface 61 that is positioned directly above the wedge 22 and makes rolling contact with the inner peripheral surface 13 of the through-hole 6 formed in the plate material 5. The movable roller 26 is urged so that the rolling contact surface 61 of the movable roller 26 and the inner peripheral surface 13 of the plate material 5 approach each other in the longitudinal direction.

The pair of fixed rollers 27 are provided one on each side of the movable roller 26 in the radial direction of the rotation shaft of the movable roller 26, or in other words, on both sides thereof in the horizontal direction. Like the movable roller 26, the pair of fixed rollers 27 are attached to the lower side of the upper plate 36a of the upper frame 36. Here, each of the fixed rollers 27 has its rotation shaft fixed to the upper plate 36a. Each of the fixed rollers 27 has a circular pillar shape, and like the movable roller 26, has a rolling contact surface 62 that makes rolling contact with the inner peripheral surface 13 of the through-hole 6 formed in the plate material 5.

The encoder 28 is connected to the rotation shaft of one of the fixed rollers 27, and is capable of detecting a rotational position of the fixed roller 27. The encoder 28 employs a rotary encoder, for example, and is connected to the control unit 30. The encoder 28 outputs data regarding the rotational position of the fixed roller 27 to the control unit 30.

The handle 29 is attached to the upper frame 36, and is provided on the side opposite from the wedge 22 in the longitudinal direction. The handle 29 is formed having a bar shape extending in the vertical direction, and is gripped by an inspector.

The control unit 30 is connected to the probe 21 and the encoder 28, and controls the ultrasonic waves emitted from the probe 21, obtains data regarding the rotational position of the fixed roller 27 outputted from the encoder 28, and so on. Specifically, the control unit 30 executes the flaw detection by the probe 21 on the basis of the rotational position of the fixed roller 27. The control unit 30 also associates a predetermined rotational position of the fixed roller 27 with a result of detecting flaws in the chamfered surface 10. Through this, the control unit 30 can expand detection results in the width direction of the chamfered surface 10 in the length direction of the chamfered surface 10. Accordingly, the control unit 30 is capable of mapping the result of detecting flaws in the chamfered surface 10 two-dimensionally in the width direction and the length direction of the chamfered surface 10.

With the ultrasonic testing device 1 configured as described above, the contact surface 51 of the wedge guide 23 is brought into contact with the outer plate surface 11 of the plate material 5, and the movable roller 26 and the pair of fixed rollers 27 are brought into contact with the inner peripheral surface 13 of the through-hole 6. Furthermore, with the ultrasonic testing device 1, the detecting surface 45 of the wedge 22 is brought into contact with the chamfered surface 10 of the plate material 5, and the spring member 25 applies an urging force causing the wedge 22 to move toward the chamfered surface 10. By making contact in this manner, the longitudinal direction of the ultrasonic testing device 1 matches the width direction of the chamfered surface 10 and the horizontal direction of the ultrasonic testing device 1 matches the length direction of the chamfered surface 10. Accordingly, the wedge guide 23 makes contact with the outer plate surface 11 of the plate material 5, and thus the position in the vertical direction of the ultrasonic testing device 1 relative to the plate material 5 is regulated. Furthermore, the movable roller 26 and the pair of fixed rollers 27 make contact with the inner peripheral surface 13 of the through-hole 6, and thus the position in the longitudinal direction of the ultrasonic testing device 1 relative to the plate material 5 is regulated.

The ultrasonic testing device 1 is moved along the length direction of the chamfered surface 10 while maintaining the aforementioned state of contact. At this time, because the urging force causing the wedge 22 to move toward the chamfered surface 10 is applied to the wedge 22 by the spring member 25, the wedge 22 can move so as to conform to the shape of the chamfered surface 10. Furthermore, the fixed rollers 27 make contact with the inner peripheral surface 13 of the through-hole 6, and thus the control unit 30 executes the flaw detection using the probe 21 at a predetermined timing based on the rotational position of the encoder 28 connected to the fixed roller 27. The control unit 30 then associates the rotational position detected by the encoder 28 with the flaw detection result from the probe 21 and stores this information as two-dimensionally mapped flaw detection data.

When the movable roller 26 and the pair of fixed rollers 27 make rolling contact along the inner peripheral surface 13, the movable roller 26 moves in the longitudinal direction in accordance with the radius of curvature of the curved inner peripheral surface 13, even when that radius of curvature changes. It is therefore possible for the movable roller 26 and the pair of fixed rollers 27 to make rolling contact with the inner peripheral surface 13 while conforming thereto.

Next, the angle of attachment of the probe 21 in the ultrasonic testing device 1 will be described with reference to FIG. 4. Note that the vertical direction in FIG. 4 is opposite from the vertical direction in FIG. 1. As described above, the probe 21 irradiates the plate material 5 with ultrasonic waves, across both the chamfered surface 10 and the outer plate surface 11.

Here, as illustrated in FIG. 4, the sonic velocity of the ultrasonic waves emitted from the transceiving surface 55 of the probe 21, or in other words, the sonic velocity of the ultrasonic waves propagating through the water that serves as the propagation couplant, is represented by $V_1$. Meanwhile, the sonic velocity of the ultrasonic waves propagating within the plate material 5 is represented by $V_2$. At this time, the sonic velocity $V_1$ of the ultrasonic waves and the sonic velocity $V_2$ of the ultrasonic waves are different sonic velocities. Meanwhile, an angle of incidence from the water into the plate material 5 is represented by $\theta$, and an angle of diffraction from the water to the plate material 5 is represented by $\beta$. In this case, based on Snell's law, the following Formula (1) holds true.

$$\sin \theta / \sin \beta = V_1 / V_2 \qquad (1)$$

As described above, the angle formed between the transceiving surface 55 of the probe 21 and the chamfered surface 10 of the plate material 5 is different from the angle formed between the transceiving surface 55 of the probe 21 and the outer plate surface 11 of the plate material 5. In addition, while the outer plate surface 11 and the inner plate surface 12 are parallel, the chamfered surface 10 and the inner plate surface 12 are not parallel. At this time, an outbound path along which the ultrasonic waves emitted from each ultrasonic element 56 in the probe 21 travel within the plate material 5 and strike the inner plate surface 12, and an inbound path along which the ultrasonic waves reflected by the inner plate surface 12 of the plate material 5 travel within the plate material 5 and enter each ultrasonic element 56, are the same path. The ultrasonic waves with which the outer plate surface 11 is irradiated and the ultrasonic waves with which the chamfered surface 10 is irradiated will be described next.

When the outer plate surface 11 is irradiated with ultrasonic waves, the outer plate surface 11 and the inner plate surface 12 are parallel. Here, in the case where the propagation direction of the ultrasonic waves is orthogonal to the inner plate surface 12, the ultrasonic waves with which the outer plate surface 11 is irradiated are to enter the outer plate surface 11 orthogonally. Thus with respect to the ultrasonic waves with which the outer plate surface 11 is irradiated, it is not necessary to take changes in the sonic velocity caused by the refractive index into consideration, even if the sonic velocity $V_1$ of the ultrasonic waves propagating within the water is different from the sonic velocity $V_2$ of the ultrasonic waves propagating within the plate material 5.

On the other hand, when the chamfered surface 10 is irradiated with ultrasonic waves, the chamfered surface 11 and the inner plate surface 12 are not parallel. Here, in the case where the propagation direction of the ultrasonic waves is orthogonal to the inner plate surface 12, the ultrasonic waves with which the chamfered surface 10 is irradiated are to enter the chamfered surface 10 such that substituting the sonic velocity $V_1$ of the ultrasonic waves propagating within the water, the sonic velocity $V_2$ of the ultrasonic waves propagating within the plate material 5, and the angle of diffraction $\beta$ from the water to the plate material 5 in Formula (1) results in the angle of incidence $\theta$. Thus with respect to the ultrasonic waves with which the chamfered surface 10 is irradiated, it is necessary to take changes in the sonic velocity caused by the refractive index into consideration in light of the sonic velocity $V_1$ of the ultrasonic waves propagating within the water being different from the sonic velocity $V_2$ of the ultrasonic waves propagating within the plate material 5.

Accordingly, the sonic velocity $V_1$ of the ultrasonic waves with which the outer plate surface 11 is irradiated is the same sonic velocity as the sonic velocity $V_1$ of the ultrasonic waves with which the chamfered surface 10 is irradiated. On the other hand, the sonic velocity $V_1$ of the ultrasonic waves with which the outer plate surface 11 is irradiated is a different sonic velocity from the sonic velocity $V_2$ of the ultrasonic waves with which the outer plate surface 11 is irradiated and that propagate within the plate material 5. Likewise, the sonic velocity $V_1$ of the ultrasonic waves with which the chamfered surface 10 is irradiated is a different sonic velocity from the sonic velocity $V_2$ of the ultrasonic waves with which the chamfered surface 10 is irradiated and that propagate within the plate material 5.

Accordingly, the probe 21 is caused to emit the ultrasonic waves so that the ultrasonic waves $V_1$ with which the outer plate surface 11 is irradiated and the ultrasonic waves $V_1$ with which the chamfered surface 10 is irradiated fulfill the aforementioned relationship, or in other words, in a state where the angle of incidence $\theta$ is calculated so that the ultrasonic waves are emitted in a direction orthogonal to the inner plate surface 12 and the angle of attachment is set such that the calculated angle of incidence $\theta$ is achieved. Then, the control unit 30 obtains a signal of the ultrasonic waves by the probe 21 receiving the ultrasonic waves reflected from the inner plate surface 12.

Next, an ultrasonic testing method using the portable ultrasonic testing device 1 described above will be described with reference to FIG. 5. Note that flaw detection using the portable ultrasonic testing device 1 may be carried out when the plate material 5 is manufactured, or may be carried out during a periodic inspection after the plate material 5 has been delivered.

First, in the case where flaws are to be detected in the chamfered surface 10 of the plate material 5, an inspector grips the handle 29 of the portable ultrasonic testing device 1. In this state, the inspector manipulates the ultrasonic testing device 1 so that the wedge guide 23 is brought into contact with the outer plate surface 11 of the plate material 5, and the movable roller 26 and the pair of fixed rollers 27 are brought into contact with the inner peripheral surface 13 of the through-hole 6. Once the rollers 26 and 27 are in contact with the inner peripheral surface 13, the ultrasonic testing device 1 is moved so that the wedge 22 approaches the chamfered surface 10 in the longitudinal direction. The wedge 22 of the ultrasonic testing device 1 makes contact with the chamfered surface 10, and then moves in the longitudinal direction toward the device frame 20 against the urging force of the spring member 25. As a result, the wedge 22 is in contact with the chamfered surface 10, with the urging force of the spring member 25 applied to the wedge 22. Accordingly, in the portable ultrasonic testing device 1, the wedge guide 23 makes contact with the outer plate surface 11 of the plate material 5, the movable roller 26 and the pair of fixed rollers 27 make contact with the inner peripheral surface 13 of the through-hole 6, and the wedge 22 makes contact with the chamfered surface 10 of the plate material 5 (step S1: a contact step). By making contact in this manner, the longitudinal direction of the ultrasonic testing device 1 matches the width direction of the chamfered surface 10 and the horizontal direction of the ultrasonic testing device 1 matches the length direction of the chamfered surface 10.

Next, the portable ultrasonic testing device 1 is moved along the length direction of the chamfered surface 10, or in other words, in the horizontal direction of the ultrasonic testing device 1 by the inspector while maintaining contact with the plate material 5 (step S2: a movement step). Accordingly, the wedge guide 23 slides on the outer plate surface 11 of the plate material 5, the wedge 22 slides on the chamfered surface 10 of the plate material 5, and the movable roller 26 and the pair of fixed rollers 27 make rolling contact with the inner peripheral surface 13 of the through-hole 6. The ultrasonic testing device 1 then detects flaws within the plate material 5 under the chamfered surface 10 using the probe 21 by operating in tandem with the movement of the ultrasonic testing device 1.

When the ultrasonic testing device 1 moves in the length direction thereof, there are cases where the ultrasonic testing device 1 moves in the width direction of the chamfered surface 10 (the longitudinal direction of the ultrasonic testing device 1), the position of the chamfered surface 10 in the width direction changes, and so on. In this case, because the wedge 22 is urged by the spring member 25, the wedge 22 can stay in contact with the chamfered surface 10. The wedge 22 can move while conforming to the shape of the chamfered surface 10 as a result.

As described thus far, according to the configuration of the present embodiment, the movable roller 26 and the pair of fixed rollers 27 can be brought into contact with the inner peripheral surface 13 of the through-hole 6, the wedge 22 can be brought into contact with the chamfered surface 10 of the plate material 5, and the spring member 25 can apply the urging force to the wedge 22. Accordingly, the wedge 22 can be kept in contact with the chamfered surface 10, and thus even if the wedge 22 is moved along the chamfered surface 10 while the movable roller 26 and the pair of fixed rollers 27 are in contact with the plate material 5, the positional relationship between the chamfered surface 10 of the plate material 5 and the probe 21 fixed to the wedge 22 can be maintained. Through this, the probe 21 can move in a favorable manner along the shape of the chamfered surface 10, and thus flaws within the plate material 5 can be detected with a high level of accuracy.

In addition, according to the configuration of the present embodiment, the wedge guide 23 can be brought into contact with the outer plate surface 11 of the plate material 5, and thus the position of the ultrasonic testing device 1 in the vertical direction indicated in FIG. 3 can be regulated. Accordingly, by bringing the wedge guide 23 into contact with the outer plate surface 11 of the plate material 5, the positional relationship between the chamfered surface 10 of the plate material 5 and the transceiving surface 55 of the probe 21 in the vertical direction can be maintained more favorably, even in the case where the wedge 22 is moved along the chamfered surface 10.

In addition, according to the configuration of the present embodiment, the wedge guide 23 can be formed having a broad shape that widens on both sides of the wedge 22, and thus the surface area across which the outer plate surface 11 of the plate material 5 and the contact surface 51 of the wedge guide 23 make contact can be increased. Accordingly, the plate material 5 and the wedge guide 23 can be brought into stable contact with each other, and thus the wedge 22 can be moved along the chamfered surface 10 in a stable manner.

In addition, according to the configuration of the present embodiment, the chamfered surface 10 formed at the peripheral edge portion of the through-hole 6 in the plate material 5 serves as the surface to be inspected, and thus flaws within the plate material 5 under the chamfered surface 10 can be detected with a high level of accuracy.

In addition, according to the configuration of the present embodiment, the plate material 5 is formed using a composite material, and thus flaws within the plate material 5 under the chamfered surface 10 can be detected with a high level of accuracy even if the material has acoustical anisotropy.

In addition, according to the configuration of the present embodiment, bringing the movable roller 26 and the pair of fixed rollers 27 into rolling contact with the inner peripheral surface 13 of the through-hole 6 in the plate material 5 makes it possible to reduce contact resistance when moving the ultrasonic testing device 1, and thus the device can be moved along the inner peripheral surface 13 smoothly.

In addition, according to the configuration of the present embodiment, even if the inner peripheral surface 13 of the through-hole 6 is a curved surface having a varying radius of curvature, the movable roller 26 present between the pair of fixed rollers 27 moves in the longitudinal direction in accordance with the radius of curvature, and thus the movable roller 26 and the pair of fixed rollers 27 can be moved along the inner peripheral surface 13 in a favorable manner.

In addition, according to the configuration of the present embodiment, connecting the fixed roller 27 to the encoder 28 makes it possible to associate the rotational position detected by the encoder 28 with the flaw detection result obtained by the probe 21 at that rotational position. Accordingly, the flaw detection result from the probe 21 can be expanded in the length direction of the chamfered surface 10 and mapped. In the present embodiment, the probe 21 is an array-type probe constituted of a plurality of ultrasonic elements 56, and thus a two-dimensional map expanded in the width direction and the length direction of the chamfered surface 10 is generated. However, in the case where the probe 21 is constituted of a single ultrasonic element 56, a linear map extending in the length direction of the chamfered surface 10 is generated.

In addition, according to the configuration of the present embodiment, the water storage unit 46 is formed as a depression with respect to the detecting surface 45 of the wedge 22. Accordingly, the water serving as the propagation couplant can be located between the transceiving surface 55 of the probe 21 and the chamfered surface 10 of the plate material 5. As a result, no gap is formed between the wedge 22 and the plate material 5, which makes it possible to suppress the sonic velocity from varying due to such a gap. Accordingly, a drop in the flaw detection accuracy due to variations in the sonic velocity can be suppressed.

In addition, according to the configuration of the present embodiment, the chamfered surface 10 can be irradiated with ultrasonic waves across the width direction thereof using the array-type probe 21 in which the plurality of ultrasonic elements 56 are arranged. Accordingly, flaws within the plate material 5 under the chamfered surface 10 can be detected with efficiency by moving the wedge 22 along the chamfered surface 10 in the length direction, and thus the flaw detection operation can be simplified.

In addition, according to the configuration of the present embodiment, in the case where the probe 21 emits the ultrasonic waves across both the chamfered surface 10 and the outer plate surface 11, the angle formed between the transceiving surface 55 of the probe 21 and the chamfered surface 10 of the plate material 5 is a different angle from the angle formed between the transceiving surface 55 of the probe 21 and the outer plate surface 11 of the plate material 5. At this time, the sonic velocity $V_1$ of the ultrasonic waves with which the outer plate surface 11 is irradiated is a different sonic velocity from the sonic velocity $V_2$ of the ultrasonic waves with which the outer plate surface 11 is irradiated and that propagate within the plate material 5. Likewise, the sonic velocity $V_1$ of the ultrasonic waves with which the chamfered surface 10 is irradiated is a different sonic velocity from the sonic velocity $V_2$ of the ultrasonic waves with which the chamfered surface 10 is irradiated and that propagate within the plate material 5. Accordingly, the probe 21 can calculate the angle of incidence θ on the basis of Formula (1) using the sonic velocity $V_1$ of the ultrasonic waves in the propagation couplant (water), the sonic velocity $V_2$ of the ultrasonic waves in the plate material 5, and the angle of diffraction β, and can emit the ultrasonic waves so as to achieve that angle of incidence θ. As such, according to the present embodiment, the probe 21 can be attached taking into consideration variations in the sonic velocity caused by the refractive index between the water and the plate material 5, and thus flaws in the plate material 5 under the chamfered surface 10 can be detected at a high level of accuracy.

Although flaw detection is carried out by the ultrasonic testing device 1 taking the chamfered surface 10, which has an elliptical shape, as the surface to be inspected in the present embodiment, the shape of the surface to be inspected is not particularly limited. The chamfered surface 10 may be formed having a circular shape, or may be formed having a shape that extends linearly in a predetermined direction.

Furthermore, although the rollers 26 and 27 are employed as members that make rolling contact with the inner peripheral surface 13 of the through-hole 6 in the present embodiment, the invention is not limited to this configuration. For example, a ball roller may be employed as the member that makes rolling contact with the inner peripheral surface 13 of the through-hole 6. In addition, a member that slides on the inner peripheral surface 13 of the through-hole 6 may be used, and a member that makes linear contact or point contact with the inner peripheral surface 13 may be applied, instead of the rollers 26 and 27.

In addition, although water is employed as the propagation couplant in the present embodiment, a propagation couplant having a sonic velocity close to that of the composite material that constitutes the plate material 5 may be employed instead of water. In this case, it is not necessary to take into consideration variations in the sonic velocity caused by the refractive index at the outer plate surface 11 and the chamfered surface 10.

Figure 6:
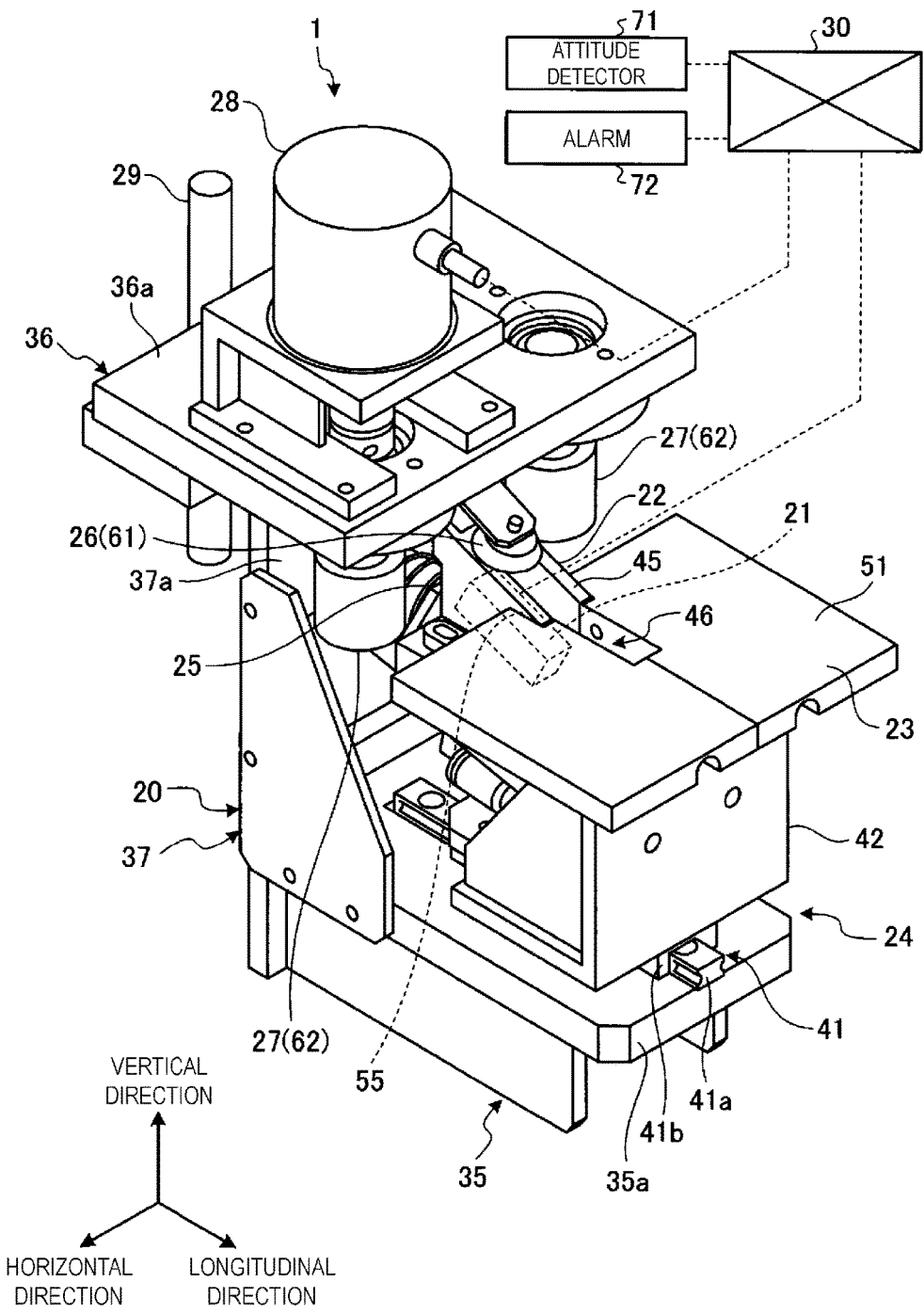
FIG. 6 is a perspective view of a portable ultrasonic testing device according to a modification.

The ultrasonic testing device 1 according to the present embodiment may be implemented as the modification illustrated in FIG. 6. FIG. 6 is a perspective view of a portable ultrasonic testing device according to the modification. As illustrated in FIG. 6, the ultrasonic testing device 1 according to the modification includes an attitude detector 71 and an alarm 72 in addition to the configuration of the present embodiment.

The attitude detector 71 is attached to the wedge 22 and measures an attitude of the probe 21. The attitude detector 71 is connected to the control unit 30. For example, an accelerometer, a gyrosensor, or the like is used as the attitude detector 71, and two- or three-axis attitude detector 71 may be used in accordance with the attitude of the probe 21 to be measured. Upon measuring the attitude of the probe 21, the attitude detector 71 outputs a measurement result to the control unit 30.

The alarm 72 emits a warning in the case where the positional relationship between the chamfered surface 10 of the plate material 5 and the transceiving surface 55 of the probe 21 is a positional relationship not suitable for flaw detection. Here, a positional relationship where, relative to the chamfered surface 10 of the plate material 5, the transceiving surface 55 of the probe 21 is positionally shifted in the direction of rotation (a roll direction) central to an axis orthogonal to the chamfered surface 10, is an example of a positional relationship not suitable for flaw detection. A positional relationship where the angle formed between the chamfered surface 10 of the plate material 5 and the transceiving surface 55 of the probe 21 is greater than a pre-set predetermined angle and is positionally shifted in a tilt direction (an angle direction) is another example of a positional relationship not suitable for flaw detection. The alarm 72 is connected to the control unit 30. For example, a lamp, a speaker, or the like is used for the alarm 72.

Upon determining on the basis of the measurement result from the attitude detector 71 that the attitude of the probe 21 is positionally shifted in the roll direction or the angle direction, the control unit 30 causes the alarm 72 to operate and emit a warning to the inspector.

As described thus far, according to the configuration of the modification, in the case where the attitude of the probe 21 is not suitable for flaw detection, that information can be communicated to the inspector by the alarm 72. Accordingly, the flaw detection can be suppressed from being carried out at an attitude not suitable for flaw detection, which makes it possible to carry out the flaw detection correctly. Note that the configuration may be such that the attitude of the probe 21 (or the wedge 22) is adjusted automatically or manually in accordance with the measurement result from the attitude detector 71.

REFERENCE SIGNS LIST

1 Ultrasonic testing device
5 Plate material
6 Through-hole
10 Chamfered surface
11 Outer plate surface
12 Inner plate surface
13 Inner peripheral surface
20 Device frame
21 Probe
22 Wedge
23 Wedge guide
24 Slide mechanism
25 Spring member
26 Movable roller
27 Fixed roller
28 Encoder
29 Handle
30 Control unit
41 Linear slider
42 Slide platform
45 Detecting surface 46 Water storage unit
51 Contact surface
55 Transceiving surface
56 Ultrasonic element
71 Attitude detector
72 Alarm

The invention claimed is:

1. A portable ultrasonic testing device for inspecting an object to be inspected, the object to be inspected having first and second surfaces and a surface to be inspected connecting the first and second surfaces, the surface to be inspected being exposed outside, the portable ultrasonic testing device configured to irradiate the surface to be inspected with ultrasonic waves while moving along the surface to be inspected so as to detect flaws in the object to be inspected, the device comprising:
a device frame;
a probe configured to irradiate the surface to be inspected with ultrasonic waves and receive reflected ultrasonic waves, wherein the surface to be inspected is a chamfered surface formed by chamfering an edge where the first surface and the second surface orthogonal to said first surface intersect, and the surface to be inspected is arranged to form a predetermined angle to the first surface;
a wedge to which the probe is fixed and which has a detecting surface configured to come in contact with the surface to be inspected;
a wedge guide moveable, with respect to the device frame, in a sliding direction along with the wedge and having a first contact surface configured to come into contact with the first surface, wherein the sliding direction is a longitudinal direction in which the wedge and the surface to be inspected move toward or away from each other;
a slide mechanism configured to move the wedge guide in the sliding direction and where the detecting surface is arranged to form the predetermined angle to the first contact surface;
an urging member that urges the detecting surface of the wedge so that the detecting surface of the wedge and the surface to be inspected approach each other in the sliding direction; and
a guide member that is provided in the device frame and includes a rolling contact member, the guide member having a second contact surface configured to come into contact with the second surface, the guide member configured to make rolling contact with said second surface, and the guide member urged toward said second surface with respect to the sliding direction.

2. The portable ultrasonic testing device according to claim 1, wherein
the wedge guide is provided extending on both sides of the wedge in an orthogonal direction orthogonal to the sliding direction within the first contact surface.

3. The portable ultrasonic testing device according to claim 1, wherein
the object to be inspected is a plate material in which a through-hole is formed;
the first surface is a plate surface of the plate material;
the second surface is an inner peripheral surface of the through-hole; and
the surface to be inspected is the chamfered surface formed by chamfering a peripheral edge of the through-hole.

4. The portable ultrasonic testing device according to claim 1, wherein
the object to be inspected is a composite material.

5. The portable ultrasonic testing device according to claim 1, wherein
the rolling contact member includes:
a movable roller provided in the device frame, the movable roller including a rotation shaft that moves in the same direction as the sliding direction; and
a pair of fixed rollers provided in the device frame so as to be located on both sides of the rotation shaft of the movable roller in a radial direction, the fixed rollers including fixed rotation shafts.

6. The portable ultrasonic testing device according to claim 1, further comprising a rotational position detector that is connected to the rolling contact member and is capable of detecting a rotational position of the rolling contact member.

7. The portable ultrasonic testing device according to claim 1, wherein
the device further comprises a medium storage unit that is formed as a depression with respect to the detecting surface of the wedge and that holds a propagation couplant to be located between the probe and the surface to be inspected.

8. The portable ultrasonic testing device according to claim 1, wherein
the probe is an array-type probe in which ultrasonic elements that transmit and receive ultrasonic waves are arranged in a direction that connects the first surface and the second surface.

9. The portable ultrasonic testing device according to claim 8, wherein
the probe emits the ultrasonic waves across both the surface to be inspected and the first surface, and irradiates the surface to be inspected with the ultrasonic waves so as to achieve an angle of incidence calculated on the basis of a sonic velocity of the ultrasonic waves with which the surface to be inspected is irradiated, a sonic velocity of the irradiated ultrasonic waves propagate within the object to be inspected, and an angle of diffraction at the surface to be inspected.

10. The portable ultrasonic testing device according to claim 1, further comprising an attitude detector that measures an attitude of the probe; and
an alarm that, on the basis of a measurement result from the attitude detector, makes a notification that the attitude of the probe with respect to the surface to be inspected of the object to be inspected is not suitable for flaw detection.

11. An ultrasonic testing method that detects flaws in the object to be inspected having the surface to be inspected using the ultrasonic testing device according to claim 1, the method comprising:
a contact step of bringing the second contact surface of the guide member into contact with the second surface of the object to be inspected, bringing the wedge into contact with the surface to be inspected of the object to be inspected, and applying an urging force to the wedge using the urging member; and
a movement step of moving the wedge along the surface to be inspected while the wedge and the guide member are in contact with the object to be inspected.

* * * * *